US011285208B2

(12) United States Patent
Mitsunaga et al.

(10) Patent No.: US 11,285,208 B2
(45) Date of Patent: Mar. 29, 2022

(54) THERAPEUTIC AGENTS FOR PANCREATIC CANCER (71) Applicants: NATIONAL CANCER CENTER, Tokyo (JP); CHUGAI SEIYAKU KABUSHIKI KAISHA, Tokyo (JP)

(72) Inventors: Shuichi Mitsunaga, Chiba (JP); Atsushi Ochiai, Chiba (JP); Masafumi Ikeda, Chiba (JP)

(73) Assignees: NATIONAL CANCER CENTER, Tokyo (JP); CHUGAI SEIYAKU KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 15/955,960

(22) Filed: Apr. 18, 2018

(65) Prior Publication Data
US 2018/0236068 A1    Aug. 23, 2018

Related U.S. Application Data (63) Continuation of application No. 14/878,163, filed on Oct. 8, 2015, now abandoned, which is a continuation of application No. 13/700,594, filed as application No. PCT/JP2011/062191 on May 27, 2013, now abandoned.

(30) Foreign Application Priority Data

May 28, 2010  (JP) ................................ 122838/2010

(51) Int. Cl.
*A61K 39/395* (2006.01)
*A61K 31/7068* (2006.01)
*A61K 45/06* (2006.01)
*C07K 16/28* (2006.01)
*A61K 39/00* (2006.01)

(52) U.S. Cl.
CPC ...... *A61K 39/3955* (2013.01); *A61K 31/7068* (2013.01); *A61K 45/06* (2013.01); *C07K 16/2866* (2013.01); *A61K 2039/505* (2013.01); *C07K 2317/24* (2013.01)

(58) Field of Classification Search
CPC .............. A61K 45/06; A61K 2039/505; A61K 39/3955; A61K 31/7068; A61K 38/204; A61K 39/00114; C07K 2317/24; C07K 16/28

See application file for complete search history.

(56) References Cited

U.S. PATENT DOCUMENTS

2007/0036785 A1   2/2007  Kishimoto et al.
2010/0129357 A1   5/2010  Garcia-Martinez et al.

FOREIGN PATENT DOCUMENTS

| CA | 2728243 A1   | 12/2009 |
|----|--------------|---------|
| EP | 0628639 A1   | 12/1994 |
| EP | 0783893 A1   | 7/1997  |
| EP | 0983767 A1   | 3/1998  |
| EP | 1074268 A1   | 2/2001  |
| EP | 1108435 A1   | 6/2001  |
| EP | 1374900 A1   | 1/2004  |
| EP | 1967209 A1   | 9/2008  |
| JP | 2007277242 A | 10/2007 |
| JP | 2007518709 A | 12/2007 |
| WO | 9219759 A1   | 4/1992  |
| WO | 9611020 A1   | 6/1995  |
| WO | 9612503 A1   | 10/1995 |
| WO | 9842377 A1   | 3/1998  |
| WO | 9947170 A1   | 3/1999  |
| WO | 0010607 A1   | 8/1999  |
| WO | 023492 A1    | 2/2001  |
| WO | 02080969 A1  | 4/2002  |
| WO | 2005059133 A3| 12/2004 |
| WO | 2007113648 A2| 3/2007  |
| WO | 2009148148 A1| 6/2009  |
| WO | 2009028150 A1| 8/2009  |

OTHER PUBLICATIONS

Kakuta,Kentaro et al., "Tangan Seitai No Men'Eki Yokuseisei, CD11B+GR-1+ Mijuku Myeloid Saibogun No Dotei to Sentakuteki Jokyoho Ni Yoru Gan Chiryo Koka No Zokyo", Japanese Association of Cancer Immunology Sokai Program, Shorokushu, vol. 14, No. 83, 2010.

Hirano, T. et al., "Complementary DNA for a Novel Human Interleukin (BSF-2) That Induces Blymphocytes to Produce Immunoglobulin", Nature, vol. 324, pp. 73-76, 1986.

Akira, S. et al., "Interleukin-6 in Biology and Medicine", Advances in Immunology, vol. 54, pp. 1-78, 1993.

Lotz, M. et al., "B Cell Stimulating Factor 2/Interleukin 6 Is a Costimulant for Human Thymocytes and T Lymphocytes", Journal of Experimental Medicine, vol. 167, pp. 1253-1258, 1988.

Taga, T. et al., "Receptors for B Cell Stimulatory Factor 2", Journal of Experimental Medicine, vol. 166, pp. 967-981, 1987.

Yamasaki, K. et al., "Cloning and Expression of the Human Interleukin-6 (BSF-2/IFN BETA 2) Receptor", Science, vol. 241, pp. 825-828, 1987.

Taga, T. et al., "Interleukin-6 Triggers the Association of Its Receptor With a Possible Signal Transducer, GP130", Cell, vol. 58, pp. 573-581, 1989.

English translation of WO09/148, 148, translated on Oct. 1, 2013.

Burrus, H.A., et al. Improvements in survival and clinical benefit with gemcitabine as first-line therapy for patients with advanced pancreas cancer: a randomized trial. J. Clin. Oncol., 1997, vol. 15, No. 6, p. 2403-2413.

(Continued)

*Primary Examiner* — Prema M Mertz
(74) *Attorney, Agent, or Firm* — Browdy and Neimark, PLLC (57) ABSTRACT

We achieved the present invention on the basis of the finding that an excellent therapeutic effect against pancreatic cancer can be obtained by administering an IL-6 inhibitor and an antimetabolite to pancreatic cancer patients. We also found that metastatic lesions from human pancreatic cancer can be reduced and ascites can be eliminated.

6 Claims, 3 Drawing Sheets

(56) References Cited

OTHER PUBLICATIONS

Extended European Search Report in corresponding European application No. 11786743.2 dated Jan. 7, 2014.
Cunningham, et al., Phase III Randomized Comparison of Gemcitabine Versus Gemcitabine Plus Capecitabine in Patients With Advanced Pancreatic Cancer, Journal of Clinical Oncology, Nov. 20, 2009, pp. 5513-5518, vol. 27, No. 33.
Ducreiux, et al., Abstract Only, A randomised trial comparing 5-FU with 5-FU plus cisplatin in advanced pancreatic carcinoma, Ann. Oncol., Aug. 2002, pp. 1185-1191, vol. 13(8).
Gansauge, et al., Abstract only, NSC-631570 (Ukrain) in the palliative treatment of pancreatic cancer. Results of a phase II trail, Langenbecks Arch Surg., Mar. 2002, pp. 570-574, vol. 386(8).
Greenway, Brian A., Effect of flutamide on survival in patients with pancreatic cancer: results of a prospective, randomised, double blind, placebo controlled trial, BMJ, Jun. 27, 1998, pp. 1935-1938, vol. 316.
Abstract only, Treatment of locally unresectable carcinoma of the pancreas: comparison of combined-modality therapy (chemotherapy plus radiotherapy) to chemotherapy alone. Gastrointestinal Tumor Study Group, J. Natl Cancer Inst., 1988, pp. 751-755, vol. 80(10).
Moore, et al., Erlotinib Plus Gemcitabine Compared With Gemcitabine Alone in Patients With Advanced Pancreatic Cancer: A Phase III Trial of the National Cancer Institute of Canada Clinical Trials Group, Journal of Clinical Oncology, May 20, 2007, pp. 1960-1966, vol. 25, No. 15.
Okusaka, et al., Abstract only, A late phase II study of S-1 for metastatic pancreatic cancer, Cancer Chemother Pharmacol, Apr. 2008, pp. 615-621, vol. 61(4).
Reni, et al., Gemcitabine versus cisplatin, epirubicin, fluorouracil, and gemcitabine in advanced pancreatic cancer: a randomised controlled multicentre phase III trial, Lancet Oncol, 2005, pp. 369-376, vol. 6.
Topham, et al., Randomised trial of epirubicin alone versus 5-fluorouracil, epirubicin and mitomycin C in locally advanced and metastatic carcinoma of the pancreas, Br. J. Cancer, 1991, pp. 179-181, vol. 64.
Ueno, et al., Abstract Only, An early phase II study of S-2 in patients with metastatic pancreatic cancer, Oncology, 2005, pp. 171-178, vol. 68 (2-3).

THERAPEUTIC AGENTS FOR PANCREATIC CANCER

TECHNICAL FIELD

The present invention relates to therapeutic compositions for pancreatic cancer. More specifically, the present invention relates to therapeutic compositions for pancreatic cancer comprising an interleukin 6 (IL-6) inhibitor, said compositions further comprising or being administered in combination with an antimetabolite.

BACKGROUND ART

IL-6 is a cytokine also called B cell stimulating factor 2 (BSF2) or interferon β2. IL-6 was discovered as a differentiation factor involved in the activation of B lymphocytes (non-patent document 1), and then demonstrated to be a multifunctional cytokine that influences functions of various cells (non-patent document 2). IL-6 has been reported to induce maturation of T lymphocytes (non-patent document 3).

IL-6 mediates its biological activities through two proteins on cells. One is the IL-6 receptor that is a ligand-binding protein having a molecular weight of about 80 kD to which IL-6 binds (non-patent document 4, non-patent document 5). The IL-6 receptor occurs as not only a membrane-bound receptor that traverses the cell membrane and is expressed on the cell membrane but also soluble IL-6 receptor mainly consisting of the extracellular domain.

The other is gp130 that is a non-ligand-binding membrane-bound protein having a molecular weight of about 130 kD involved in signal transduction. IL-6 and the IL-6 receptor form an IL-6/IL-6 receptor complex and subsequently bind to gp130, thereby mediating biological activities of IL-6 into cells (non-patent document 6).

Patent document 1 describes various forms of anti-IL-6 (IL-6 receptor) antibodies such as humanized anti-IL-6 antibodies, chimeric anti-IL-6 antibodies and the like. Patent document 2 describes therapeutic agents for chronic rheumatoid arthritis and synovial cell growth inhibitors containing IL-6 antagonists such as anti-IL-6 antibodies as active ingredients. Patent document 3 describes treatment of diseases caused by IL-6 production such as plasmacytosis, hyperimmunoglobulinemia, anemia, nephritis, cachexia, rheumatism, Castleman's disease, mesangium proliferative nephritis and the like. Patent document 4 describes prophylactic/therapeutic agents for sensitized T cell-mediated diseases such as multiple sclerosis, uveitis, chronic thyroiditis, delayed hypersensitivity, contact dermatitis, atopic dermatitis and the like, containing anti-IL-6 antibodies as active ingredients.

Patent document 5 describes therapeutic agents for systemic lupus erythematosus, containing anti-IL-6 antibodies as active ingredients. Patent document 6 describes therapeutic agents for Crohn's disease, containing anti-IL-6 antibodies as active ingredients. Patent document 7 describes therapeutic agents for pancreatitis containing anti-IL-6 antibodies as active ingredients. Patent document 8 describes therapeutic agents for psoriasis containing anti-IL-6 antibodies as active ingredients. Further, patent document 9 describes therapeutic agents for juvenile chronic arthritis containing anti-IL-6 antibodies as active ingredients. Patent document 10 describes inhibitors of perineural invasion by cells containing anti-IL-6 antibodies as active ingredients and describes that perineural invasion in human pancreatic cancer can be suppressed.

Gemcitabine (Gemzar®) (HCl) is a cytosine analog that inhibits DNA synthesis by inhibiting ribonucleotide reductase and competing with dCTP for incorporation into DNA. Currently, it is used as a therapeutic agent for some cancers such as pancreatic cancer. It is also used as a combination therapy with radiotherapy, but has not achieved significant improvement in extended survival of pancreatic cancer patients. Some attempts have been made for other effective combination therapies, but any improvement in survival rate has not been reported.

Pancreatic cancer is diagnosed at unresectable advanced stages in many cases even today, and associated with rapid progress and very poor prognosis. Even cases having undergone the only possible cure resection often lead to early recurrence after operation. On the other hand, chemotherapy is indicated for unresectable cases with good performance status (PS) and major organ function, but even the current standard of care does not have sufficient therapeutic effect. For example, even gemcitabine hydrochloride positioned as a first-line therapy has an efficacy in symptom palliation of 23.8%, a median survival time of 5.7 months, and a one-year survival rate of 18% (results from foreign phase III clinical trials). In Japan, 20,000 people are diagnosed with and 22,260 people die of pancreatic cancer annually (The 2004 Demographic Survey by the Ministry of Health, Labour and Welfare of Japan), and it is the fifth leading cause of cancer-related death.

Information about prior art documents related to the invention of the present application is shown below.

CITATION LIST

Non-Patent Documents

Non-patent document 1: Hirano, T. et al., Nature (1986) 324, 73-76;
Non-patent document 2: Akira, S. et al., Adv. in Immunology (1993) 54, 1-78;
Non-patent document 3: Lutz, M. et al., J. Exp. Med. (1988) 167, 1253-1258;
Non-patent document 4: Taga, T. et al., J. Exp. Med. (1987) 166, 967-981;
Non-patent document 5: Yamasaki, K. et al., Science (1987) 241, 825-828;
Non-patent document 6: Taga, T. et al., Cell (1989) 58, 573-581.

Patent Documents

Patent document 1: International Publication 092/19759;
Patent document 2: WO96/11020;
Patent document 3: WO96/12503;
Patent document 4: WO98/42377;
Patent document 5: WO99/08707;
Patent document 6: WO99/47170;
Patent document 7: WO00/10607;
Patent document 8: WO02/3492;
Patent document 9: WO02/080969;
Patent document 10: WO2009/148148.

SUMMARY OF INVENTION

Technical Problem

The present invention aims to provide a novel therapeutic agent for pancreatic cancer.

Solution to Problem

As a result of careful studies to solve the above problems, we accomplished the present invention on the basis of the finding that an excellent therapeutic effect against pancreatic cancer can be obtained by using an IL-6 inhibitor and an antimetabolite in combination in pancreatic cancer patients. We also found that metastatic lesions from human pancreatic cancer can be reduced and ascites can be eliminated by the combination described above.

Accordingly, the present invention more specifically provides [1]-[21] below.

[1] A therapeutic composition for pancreatic cancer comprising an IL-6 inhibitor, said composition further comprising an antimetabolite or being administered in combination with an antimetabolite.
[2] The therapeutic composition of [1] wherein the IL-6 inhibitor is a substance binding to the IL-6 receptor.
[3] The therapeutic composition of [2] wherein the substance binding to the IL-6 receptor is an anti-IL-6 receptor antibody.
[4] The therapeutic composition of [3] wherein the anti-IL-6 receptor antibody is a chimeric antibody, a humanized antibody or a human antibody.
[5] The therapeutic composition of any one of [1]-[4] wherein the antimetabolite is a cytosine analog.
[6] The therapeutic composition of [5] wherein the cytosine analog is gemcitabine or a salt thereof.
[7] The therapeutic composition of [6] wherein gemcitabine or a salt thereof is gemcitabine hydrochloride.
[8] A method for treating pancreatic cancer comprising the step of administering an IL-6 inhibitor and an antimetabolite to a subject.
[9] The method of [8] wherein the IL-6 inhibitor is a substance binding to the IL-6 receptor.
[10] The method of [9] wherein the substance binding to the IL-6 receptor is an anti-IL-6 receptor antibody.
[11] The method of [10] wherein the anti-IL-6 receptor antibody is a chimeric antibody, a humanized antibody or a human antibody.
[12] The method of any one of [8]-[11] wherein the antimetabolite is a cytosine analog.
[13] The method of [12] wherein the cytosine analog is gemcitabine or a salt thereof.
[14] The method of [13] wherein gemcitabine or a salt thereof is gemcitabine hydrochloride.
[15] An IL-6 inhibitor for use in a method for treating pancreatic cancer by administering it in combination with an antimetabolite.
[16] The inhibitor of [15] wherein the IL-6 inhibitor is a substance binding to the IL-6 receptor.
[17] The inhibitor of [16] wherein the substance binding to the IL-6 receptor is an anti-IL-6 receptor antibody.
[18] The inhibitor of [17] wherein the anti-IL-6 receptor antibody is a chimeric antibody, a humanized antibody or a human antibody.
[19] The inhibitor of any one of [15]-[18] wherein the antimetabolite is a cytosine analog.
[20] The inhibitor of [19] wherein the cytosine analog is gemcitabine or a salt thereof.
[21] The inhibitor of [20] wherein gemcitabine or a salt thereof is gemcitabine hydrochloride.

Advantageous Effects of Invention

An excellent therapeutic effect against pancreatic cancer was obtained by using an IL-6 inhibitor and an antimetabolite in combination. Moreover, it was shown that metastatic lesions from human pancreatic cancer can be reduced and ascites can be eliminated by the combination described above. Especially, there has been no report that ascites is eliminated by monotherapy.

DESCRIPTION OF EMBODIMENTS

As used herein, "IL-6 inhibitor" refers to a substance that blocks IL-6-mediated signal transduction to inhibit biological activities of IL-6. Specific examples of IL-6 inhibitors include substances binding to IL-6, substances binding to the IL-6 receptor, substances binding to gp130 and the like. IL-6 inhibitors also include substances inhibiting STAT3 phosphorylation that is a primary event in IL-6-mediated intracellular signaling, such as AG490. IL-6 inhibitors include, but not specifically limited to, anti-IL-6 antibodies, anti-IL-6 receptor antibodies, anti-gp130 antibodies, IL-6 variants, soluble IL-6 receptor variants, IL-6 peptides, IL-6 receptor peptides, and small molecules showing similar activities to those of these substances, etc.

Preferred examples of IL-6 inhibitors include IL-6 receptor inhibitors, especially anti-IL-6 receptor antibodies.

The origin from which antibodies used in the present invention are derived is not specifically limited, but preferably a mammal, more preferably human.

Antibodies used in the present invention can be obtained as polyclonal or monoclonal antibodies by using known means. Antibodies used in the present invention are preferably monoclonal antibodies especially derived from mammals. Monoclonal antibodies derived from mammals include those produced by hybridomas and those produced by hosts transformed with an expression vector containing an antibody gene by genetic engineering techniques. Normally, these antibodies block mediation of biological activities of IL-6 into cells by binding to IL-6, the IL-6 receptor, gp130 or the like.

Hybridomas producing monoclonal antibodies can be constructed basically using known techniques as follows. That is, the IL-6 receptor, IL-6, gp130 or the like is used as an immunizing antigen to immunize host cells according to a standard immunization technique, and the resulting immunized cells are fused to known parent cells by a standard cell fusion technique, and then the fused cells are screened for monoclonal antibody-producing cells by a standard screening method.

Specifically, monoclonal antibodies can be prepared as follows. When anti-IL-6 receptor antibodies are to be prepared, for example, the human IL-6 receptor or mouse IL-6 receptor used as an immunizing antigen for preparing the antibodies is obtained by using the nucleotide/amino acid sequence of the IL-6 receptor disclosed in European Patent Application published as EP 325474 or Japanese Patent Application published as JPA 1103-155795, respectively.

The IL-6 receptor protein occurs in two forms, i.e., one is expressed on the plasma membrane and the other is separated from the plasma membrane (soluble IL-6 receptor) (Yasukawa, K. et al., J. Biochem. (1990) 108, 673-676). The soluble IL-6 receptor differs from the membrane-bound IL-6 receptor in that it substantially consists of the extracellular domain of the IL-6 receptor bound to the plasma membrane and lacks the transmembrane domain or the transmembrane domain and the intracellular domain. Either IL-6 receptor protein can be used so far as it can be used as an immunizing antigen for preparing anti-IL-6 receptor antibodies used in the present invention.

A suitable host cell is transformed with a known expression vector system containing the nucleotide sequence of the IL-6 receptor, and then the desired IL-6 receptor protein is purified from the host cell or the culture supernatant by a known method, and this purified IL-6 receptor protein can be used as an immunizing antigen. Alternatively, a cell expressing the IL-6 receptor or a fusion protein of the IL-6 receptor protein with another protein may also be used as an immunizing antigen.

Similarly, when IL-6 is used as an immunizing antigen for preparing antibodies, the human IL-6 is obtained by using the nucleotide/amino acid sequence of IL-6 disclosed in Eur. J. Biochem (1987) 168, 543-550, J. Immunol (1988) 140, 1534-1541 or Agr. Biol. Chem. (1990) 54, 2685-2688. Further, the nucleotide/amino acid sequence of gp130 disclosed in European Patent Application published as EP 411946 can be used as an immunizing antigen for obtaining anti-gp130 antibodies.

Mammals immunized with the immunizing antigens are not specifically limited, but preferably selected on the basis of the compatibility with parent cells used for cell fusion, and rodents such as mice, rats and hamsters are typically used.

Animals are immunized with the immunizing antigens according to known methods. For example, a typical method is intraperitoneal or subcutaneous injection of an immunizing antigen into a mammal. Specifically, an immunizing antigen is preferably diluted or suspended in PBS (Phosphate-Buffered Saline) or physiological saline to an appropriate volume and, if desired, mixed with an appropriate amount of a conventional adjuvant such as Freund's complete adjuvant, and emulsified and then administered to a mammal several times every 4-21 days. A suitable vehicle can be used during immunization with the immunizing antigen.

After immunizing the mammal in this manner and confirming an increase in the serum level of a desired antibody, immunized cells are collected from the mammal and used for cell fusion. Preferred immunized cells used for cell fusion include spleen cells among others.

As for myeloma cells of the mammal used as parent cells to which the immunized cells are fused, various previously known cell lines are appropriately used such as P3X63Ag8.653 (Kearney, J. F. et al. J. Immunol (1979) 123, 1548-1550), P3X63Ag8U.1 (Current Topics in Microbiology and Immunology (1978) 81, 1-7), NS-1 (Kohler. G. and Milstein, C. Eur. J. Immunol (1976) 6, 511-519), MPC-11 (Margulies. D. H. et al., Cell (1976) 8, 405-415), SP2/0 (Shulman, M. et al., Nature (1978) 276, 269-270), FO (de St. Groth, S. F. et al., J. Immunol Methods (1980) 35, 1-21), S194 (Trowbridge, I. S. J. Exp. Med. (1978) 148, 313-323), R210 (Galfre, G. et al., Nature (1979) 277, 131-133), etc.

Cell fusion of the immunized cells to myeloma cells can be performed basically according to known methods such as the method of Milstein et al. (Kohler. G. and Milstein, C., Methods Enzymol. (1981) 73, 3-46) and the like.

More specifically, the cell fusion is performed, for example, in a conventional nutrient culture medium in the presence of a cell fusion promoter. Fusion promoters that can be used include, for example, polyethylene glycol (PEG), Sendai virus (HVJ) and the like, and, if desired, an adjuvant such as dimethyl sulfoxide can also be added to increase the fusion efficiency.

Immunized cells and myeloma cells are preferably used in a ratio of immunized cells to myeloma cells of 1-10, for example. Culture media that can be used for the cell fusion include, for example, RPMI1640 and MEM, which are well-suitable for culturing the myeloma cell lines listed above, and other conventional culture media used for this type of cell culture, optionally in combination with serum supplements such as fetal calf serum (FCS).

Cell fusion is performed by thoroughly mixing given amounts of the immunized cells and myeloma cells in the culture medium, adding a PEG solution such as a PEG solution having an average molecular weight of about 1000-6000 preheated to about 37° C. typically at a concentration of 30-60% (w/v) and mixing the suspension to form desired fused cells (hybridomas). Then, cell fusion promoters and the like that are undesirable for the growth of hybridomas can be removed by repeating the sequential steps of adding a suitable culture medium, centrifuging the suspension and removing the supernatant.

The hybridomas are selected by incubation in a conventional selective culture medium such as HAT medium (a culture medium containing hypoxanthine, aminopterin and thymidine). The incubation in the HAT medium is continued for a sufficient period to kill cells other than desired hybridomas (non-fused cells), typically several days to several weeks. Then, hybridomas producing the desired antibody are screened by conventional limiting dilution and are cloned.

As an alternative to the method for obtaining the hybridomas by immunizing a non-human animal with an antigen, a desired human antibody having a binding activity for a desired antigen protein or antigen-expressing cell can also be obtained by in vitro immunizing human lymphocytes with the desired antigen or antigen-expressing cell and fusing the immunized lymphocytes to human myeloma cells such as U266 (see JPB H01-59878). Alternatively, a desired human antibody can also be obtained by the method described above except that an antigen or antigen-expressing cell is administered to a transgenic animal harboring the human antibody gene repertoire (see International Patent Applications published as WO 93/12227, WO 92/03918, WO 94/02602, WO 94/25585, WO 96/34096, WO 96/33735).

Hybridomas producing monoclonal antibodies prepared in this manner can be subcultured in conventional culture media and stored for a long period in liquid nitrogen.

Monoclonal antibodies can be obtained from the hybridomas as culture supernatant after the hybridomas are cultured according to conventional methods or as ascites fluid after the hybridomas are grown in a mammal compatible with them. The former method is suitable for obtaining high purity antibodies while the latter method is suitable for mass production of antibodies.

For example, hybridomas producing anti-IL-6 receptor antibodies can be prepared by the method disclosed in JPA H03-139293. They can be prepared by injecting PM-1 antibody-producing hybridomas into the peritoneal cavity of a BALB/c mouse to produce ascites fluid and purifying PM-1 antibodies from this ascites fluid, or by culturing the hybridomas in a suitable culture medium such as RPMI1640 containing 10% bovine fetal serum and 5% BM-Condimed H1 (from Boehringer Mannheim), Hybridoma SFM (from GIBCO-BRL), PFHM-II (from GIBCO-BRL) or the like and purifying PM-1 antibodies from the culture supernatant.

In the present invention, recombinant antibodies produced using genetic engineering techniques by transforming a host with a suitable vector containing an antibody gene cloned from a hybridoma can be used as monoclonal antibodies (see e.g., Borrebaeck C. A. K. and Larrick J. W. THERAPEUTIC MONOCLONAL ANTIBODIES, Published in the United Kingdom by MACMILLAN PUBLISHERS LTD, 1990).

Specifically, mRNA sequences encoding the variable (V) regions of a desired antibody are isolated from cells producing the antibody such as hybridomas. Isolation of mRNA is accomplished by preparing total RNA by known methods such as guanidine ultracentrifugation (Chirgwin, J. M. et al., Biochemistry (1979) 18, 5294-5299), the AGPC method (Chomczynski, P. et al., Anal. Biochem. (1987)162, 156-159) or the like and preparing mRNA using an mRNA Purification Kit (from Pharmacia) or the like. mRNA can be directly prepared by using QuickPrep mRNA Purification Kit (from Pharmacia).

A reverse transcriptase is used to synthesize cDNA sequences of the antibody V regions from the mRNA sequences obtained. Synthesis of cDNA can be made by using AMV Reverse Transcriptase First-strand cDNA Synthesis Kit or the like. Synthesis and amplification of cDNA can be made by 5'-RACE (Frohman, M. A. et al., Proc. Natl. Acad. Sci. USA (1988) 85, 8998-9002; Belyaysky, A. et al., Nucleic Acids Res. (1989) 17, 2919-2932) using 5'-Ampli FINDER RACE Kit (from Clontech) and PCR. Desired DNA fragments are purified from the resulting PCR products and linked to vector DNA. Thus, recombinant vectors are generated and transferred into $E.\ coli$ or the like and colonies are selected to prepare desired recombinant vectors. The nucleotide sequence of the desired DNA is confirmed by known methods such as dideoxynucleotide chain termination.

Once DNA sequences encoding the V regions of the desired antibody are obtained, they are linked to DNA sequences encoding the constant regions (C regions) of the desired antibody and inserted into an expression vector. Alternatively, DNA sequences encoding the V regions of the antibody can be inserted into an expression vector containing DNA sequences of the C regions of the antibody.

To prepare antibodies used in the present invention, an antibody gene can be inserted into an expression vector in such a manner that it can be expressed under the control of expression regulatory regions such as enhancers and promoters, as described below. Then, a host cell can be transformed with this expression vector to express the antibody.

In the present invention, recombinant antibodies, i.e. antibodies artificially modified to reduce antigenicity in humans or for other purposes such as chimeric antibodies and humanized antibodies can be used. These modified antibodies can be prepared by known processes.

Chimeric antibodies can be obtained by linking DNA sequences encoding the antibody variable regions obtained as described above to DNA sequences encoding the constant regions of a human antibody and transforming a host with an expression vector containing the linked sequences to allow it to produce a recombinant antibody (see European Patent Application published as EP 125023, International Patent Application published as WO 92-19759). Chimeric antibodies useful for the present invention can be obtained by using this known method.

Humanized antibodies are also called reshaped human antibodies, and obtained by grafting the complementarity-determining regions (CDRs) of an antibody from a non-human mammal such as a mouse into the complementarity-determining regions of a human antibody and typical gene recombination techniques for preparing them are also known (see European Patent Application published as EP 125023, International Patent Application published as WO 92-19759).

Specifically, DNA sequences designed to link the CDRs of a mouse antibody to the framework regions (FRs) of a human antibody are synthesized by PCR from several oligonucleotides prepared to have terminal overlapping regions. The resulting DNA sequences are linked to DNA sequences encoding the constant regions of the human antibody and then inserted into an expression vector, which is transformed into a host to allow it to produce a recombinant antibody (see European Patent Application published as EP 239400, International Patent Application published as WO 92-19759).

The FRs of the human antibody to be linked via the CDRs are selected so that the complementarity-determining regions form an appropriate antigen-binding site. If necessary, reshaped human antibodies may have some amino acid changes in the framework regions in the variable regions of the antibodies so that the complementarity-determining regions form an appropriate antigen-binding site (Sato, K. et al., Cancer Res. (1993) 53, 851-856).

Chimeric antibodies and humanized antibodies typically use human antibody constant regions. Human antibody heavy chain constant regions that can be used include Cγ or the like such as Cγ1, Cγ2, Cγ3 or Cγ4. Human antibody light chain constant regions include, for example, κ or λ. The human antibody constant regions can be modified to improve the stability of the antibody or production thereof.

Chimeric antibodies consist of the variable regions of an antibody derived from a non-human mammal and the constant regions derived from a human antibody, while humanized antibodies consist of the complementarity determining regions of an antibody derived from a non-human mammal and the framework regions and constant regions derived from a human antibody so that they are useful as antibodies used as pharmaceuticals because of their reduced antigenicity in human bodies.

Preferred specific examples of humanized antibodies used in the present invention include humanized PM-1 antibodies (see International Patent Application published as WO 92-19759).

In addition to the methods for obtaining human antibodies described above, methods for obtaining human antibodies by panning using a human antibody library are also known. For example, phages that bind to an antigen can be selected by expressing the variable regions of a human antibody as single chain antibody fragments (scFvs) on phage surfaces by a phage display method. The DNA sequences encoding the variable regions of the human antibody that binds to the antigen can be determined by analyzing the genes of the phages selected. Once the DNA sequences of the scFvs that bind to the antigen are known, a suitable expression vector containing the sequences can be prepared to produce a human antibody. These methods have already been well known and can be found in WO 92/01047, WO 92/20791, WO 93/06213, WO 93/11236, WO 93/19172, WO 95/01438, and WO 95/15388.

The antibody gene constructed as described above can be expressed by known methods. When mammalian cells are used, the antibody gene can be expressed in a DNA sequence to which conventional useful promoters, the antibody gene to be expressed and a polyA signal downstream of or 3' to the gene are operably linked or a vector containing it. For example, promoters/enhancers include human cytomegalovirus immediate early promoter/enhancer.

Other promoters/enhancers that can be used for expressing antibodies used in the present invention include viral promoters/enhancers derived from retroviruses, polyomaviruses, adenoviruses, simian virus 40 (SV40) and the like or promoters/enhancers derived from mammalian cells such as human elongation factor 1α (HEF1α).

For example, expression can be readily accomplished according to the method of Mulligan et al. (Mulligan, R. C. et al., Nature (1979) 277, 108-114) when the SV40 promoter/enhancer is used or according to the method of Mizushima et al. (Mizushima, S. and Nagata, S. Nucleic Acids Res. (1990) 18, 5322) when the HEF1α promoter/enhancer is used.

Hosts using prokaryotic cells include producing systems using bacterial cells. Known bacterial cells include *E. coli* and *Bacillus subtilis*.

In *E. coli*, an antibody gene can be expressed by operably linking conventional useful promoters, a signal sequence for antibody secretion and the antibody gene to be expressed. For example, promoters include the lacZ promoter and araB promoter. Expression can be accomplished according to the method of Ward et al. (Ward, E. S. et al., Nature (1989) 341, 544-546; Ward, E. S. et al. FASEB J. (1992) 6, 2422-2427) when the lacZ promoter is used or according to the method of Better et al. (Better, M. et al. Science (1988) 240, 1041-1043) when the araB promoter is used.

The pelB signal sequence (Lei, S. P. et al J. Bacteriol. (1987) 169, 4379-4383) can be used as the signal sequence for antibody secretion when the antibody is to be produced in the periplasm of *E. coli*. The antibody produced in the periplasm is isolated, and then used after the structure of the antibody is suitably refolded (see e.g., WO96/30394).

An origin of replication derived from SV40, polyomaviruses, adenoviruses, bovine papillomavims (BPV) and the like can be used, and the expression vector can also contain a selectable marker such as the aminoglycoside phosphotransferase (APH) gene, thymidine kinase (TK) gene, *E. coli* xanthine-guanine phoshoribosyl transferase (Ecogpt) gene, dihydrofolate reductase (dhfr) gene or the like to amplify the gene copy number in the host cell system.

Any producing systems can be used to prepare antibodies used in the present invention. Producing systems for preparing the antibodies include in vitro and in vivo producing systems. In vitro producing systems include producing systems using eukaryotic cells and producing systems using prokaryotic cells.

Producing systems using eukaryotic cells as hosts include those using animal cells, plant cells or fungal cells. Known animal cells include (1) mammalian cells such as CHO, COS, myeloma, BHK (baby hamster kidney), HeLa and Vero cells; (2) amphibian cells such as *Xenopus oocytes*; or (3) insect sells such as sf9, sf21 and Tn5. Known plant cells include cells derived from *Nicotiana tabacumn*, which can be grown as callus cultures. Known fungal cells include yeasts such as *Saccharomyces* spp., e.g. *Saccharomyces serevisiae* and filamentous fungi such as *Aspergillus* spp., e.g. *Aspergillus niger*.

Antibodies can be obtained by transforming these cells with a desired antibody gene and culturing the transformed cells in vitro. Cultivation is performed according to known methods. For example, DMEM, MEM, RPMI1640 and IMDM can be used as culture media optionally in combination with serum supplements such as fetal calf serum (FCS). Alternatively, antibodies may be produced in vivo by transplanting cells transformed with an antibody gene into the peritoneal cavity or the like of an animal.

On the other hand, in vivo producing systems include producing systems using animals and producing systems using plants. Producing systems using animals include those using mammals, insects and the like.

Mammals that can be used include goat, pig, sheep, mouse, cow and the like (Vicki Glaser, SPECTRUM Biotechnology Applications, 1993). Insects that can be used include silkworm. Plants that can be used include, for example, tobacco.

An antibody gene is transferred into these animals or plants and antibodies are produced in vivo in the animals or plants and recovered. For example, an antibody gene is inserted midway in a gene encoding a protein produced specifically in milk such as goat β casein to prepare a fusion gene. A DNA fragment bearing the fusion gene containing the antibody gene is injected into the embryo of a goat and this embryo is implanted into a female goat. A desired antibody is obtained from the milk produced by a transgenic goat born from the goat impregnated with the embryo or progeny thereof. To increase the amount of milk containing the desired antibody produced by the transgenic goat, hormones may be used for the transgenic goat as appropriate (Ebert, K. M. et al., Bio/Technology (1994) 12, 699-702).

When silkworm is used, a desired antibody is obtained from the body fluid of silkworm infected with a baculovirus containing the gene for the desired antibody (Maeda, S. et al., Nature (1985) 315, 592-594). When tobacco is used, the gene for a desired antibody is inserted into a plant expression vector such as pMON 530, and this vector is transferred into a bacterium such as *Agrobacterium tumefaciens*. The desired antibody is obtained from leaves of tobacco such as *Nicotiana tabacum* infected with this bacterium (Julian, K.-C. Ma et al., Eur. J. Immunol. (1994) 24, 131-138).

When an antibody is to be produced in an in vitro or in vivo producing system as described above, a host may be cotransformed with expression vectors separately containing DNA sequences encoding the heavy chain (H chain) or light chain (L chain) of the antibody or may be transformed with a single expression vector containing DNA sequences encoding the heavy and light chains (see International Patent Application published as WO 94-11523).

Antibodies used in the present invention may be antibody fragments or modified products thereof so far as they can be conveniently used in the present invention. For example, antibody fragments include Fab, (Fab')$_2$, Fv, or single chain Fv (scFv) in which heavy and light chain Fv fragments are joined via a suitable linker.

Specifically, an antibody is treated with an enzyme such as papain or pepsin to produce antibody fragments or genes encoding these antibody fragments are constructed and introduced into an expression vector and then expressed in a suitable host cell (see e.g., Co, M. S. et al., J. Immunol. (1994) 152, 2968-2976, Better, M. & Horwitz, A. H. Methods in Enzymology (1989) 178, 476-496, Plueckthun, A. & Skerra, A. Methods in Enzymology (1989) 178, 497-515, Lamoyi, E., Methods in Enzymology (1989) 121, 652-663, Rousseaux, J. et al., Methods in Enzymology (1989) 121, 663-66, Bird, R. E. et al., TIBTECH (1991) 9, 132-137).

scFvs are obtained by connecting a heavy chain variable region and a light chain variable region of an antibody. In the scFvs, the heavy chain variable region and light chain variable region are connected via a linker, preferably a peptide linker (Huston, J. S. et al., Proc. Natl. Acad. Sci. U.S.A. (1988) 85, 5879-5883). The heavy chain variable region and light chain variable region in the scFvs may be derived from any of the antibodies listed above. Any single-chain peptide composed of 12-19 amino acid residues can be used, for example, as the peptide linker connecting the variable regions.

DNA sequences encoding scFvs are obtained by using a DNA sequence encoding the heavy chain or the heavy chain variable region and a DNA sequence encoding the light chain or the light chain variable region of the antibody as templates to amplify a DNA segment encoding a desired amino acid sequence of the template DNA sequences by PCR using a primer pair defining both ends of the segment, and then further amplifying a DNA sequence encoding a peptide linker segment using a primer pair defining both ends of the linker segment to be connected to the heavy chain and the light chain, respectively.

Once DNA sequences encoding scFvs are prepared, an expression vector containing them and a host transformed with the expression vector can be obtained by conventional methods, and scFvs can be obtained by using the host according to conventional methods.

These antibody fragments can be produced by the host after the genes for them are obtained and expressed in the same manner as described above. As used herein, "antibody" also means to include these antibody fragments.

Modified antibodies including antibodies conjugated with various molecules such as polyethylene glycol (PEG) can also be used. These modified antibodies are also included in the "antibody" as used herein. Such modified antibodies can be obtained by chemically modifying antibodies produced. These methods have already been established in this field of art.

Antibodies produced and expressed as described above can be isolated from cells or hosts and purified to homogeneity. Isolation and purification of antibodies used in the present invention can be performed by affinity chromatography. Columns used for affinity chromatography include, for example, protein A columns and protein G columns. Supports used for protein A columns include, for example, HyperD, POROS, Sepharose EL and the like Any other isolation/purification methods conventionally used for proteins may be used without limitation.

For example, antibodies used in the present invention can be isolated/purified by appropriately selecting and combining chromatographies other than affinity chromatography described above, filtration, ultrafiltration, salting, dialysis and the like. Chromatographies include, for example, ion exchange chromatography, hydrophobic chromatography, gel filtration chromatography and the like. These chromatographies can be applied to HPLC (High performance liquid chromatography). Reverse phase HPLC can also be used.

The concentration of the antibodies obtained above can be determined by absorbance assays or ELISA or the like. Specifically, an absorbance assay can be performed by appropriately diluting an antibody with PBS(−), then measuring the absorbance at 280 nm, and calculating the concentration on the basis that a 1 mg/ml solution has 1.35 OD. On the other hand, ELISA assay can be performed as follows. That is, 100 μl of goat anti-human IgG (from TAG) diluted to 1 μg/ml with 0.1 M bicarbonate buffer (pH 9.6) is added to a 96-well plate (from Nunc) and incubated overnight at 4° C. to immobilize the antibody. After blocking, 100 μl of an appropriately diluted antibody used in the present invention or a sample containing the antibody or human IgG standard (from CAPPEL) is added and incubated at room temperature for 1 hour.

After washing, 100 μl of 1:5000 diluted alkaline phosphatase-conjugated anti-human IgG (from BIO SOURCE) is added and incubated at room temperature for 1 hour. After washing, a substrate solution is added and incubated, and then the absorbance at 405 nm is measured using MICROPLATE READER Model 3550 (from Bio-Rad) and the concentration of the antibody of interest is calculated.

Specific examples of anti-IL-6 antibodies include, but not specifically limited to, MH166 (Matsuda, T. et al., Eur, J. Immunol. (1998) 18, 951-956), SK2 antibodies (Sato K et al., Academic Conference Proceedings of 21st Annual Meeting of Japanese Society for Immunology (1991) 21, 166), and the like.

Specific examples of anti-IL-6 receptor antibodies include, but not specifically limited to, MR16-1 (Tamura, T. et al. Proc. Natl. Acad. Sci. USA (1993) 90, 11924-11928), PM-1 antibodies (Hirata, Y. et al., J. Immunol. (1989) 143, 2900-2906), AUK12-20, AUK64-7 or AUK146-15 (International Patent Application published as WO 92-19759), etc. Among them, preferred monoclonal antibodies against the human IL-6 receptor include, but not limited to, PM-1 antibodies, and preferred monoclonal antibodies against the mouse IL-6 receptor include, but not limited to, MR16-1. A preferred example of humanized anti-IL-6 receptor antibodies includes the humanized PM-1 antibody (Tocilizumab, MRA). Other preferred examples of humanized anti-IL-6 receptor antibodies include the antibodies described in WO2009/041621. Further, additional preferred examples of anti-IL-6 receptor antibodies include anti-IL-6 receptor antibodies recognizing the same epitope as recognized by the humanized PM-1 antibody (Tocilizumab, MRA).

Specific examples of anti-gp130 antibodies include, but not specifically limited to, AM64 (Japanese Patent Application published as JPA H03-219894), 4B11, 2H4 (U.S. Pat. No. 5,571,513), B-P8 (JPA H08-291199), etc.

IL-6 variants used in the present invention are substances having binding activity for the IL-6 receptor but not mediating biological activities of IL-6. In other words, IL-6 variants bind to the IL-6 receptor competitively with IL-6, but block IL-6-mediated signal transduction because they do not mediate biological activities of IL-6.

IL-6 variants are prepared by introducing variations by changing amino acid residues of the amino acid sequence of IL-6. IL-6 variants are derived from IL-6 of any origin, but preferably human IL-6 in view of antigenicity or the like. Specifically, a variant is obtained by predicting the secondary structure of IL-6 from its amino acid sequence using a known molecular modeling program such as WHATIF (Vriend et al., J. Mol. Graphics (1990) 8, 52-56) and evaluating the influence of an amino acid residue to be changed on the complete amino acid sequence. After a suitable amino acid residue to be changed is determined, a vector containing a nucleotide sequence encoding the human IL-6 gene is used as a template to introduce a variation by conventional PCR so that the amino acid is changed, whereby a gene encoding an IL-6 variant can be obtained. This gene can be inserted into a suitable expression vector as appropriate and manipulated according to the methods for expressing, producing and purifying recombinant antibodies described above, whereby the IL-6 variant can be obtained.

Specific examples of IL-6 variants include the IL-6 variants disclosed in Brakenhoff et al., J. Biol. Chem. (1994)

269, 86-93; and Saving et al., EMBO J. (1994) 13, 1357-1367, WO 96-18648 and WO96-17869.

IL-6 receptor peptides are peptides consisting of the amino acid sequence of a part or all of the region responsible for binding of IL-6 to the IL-6 receptor in the amino acid sequence of the IL-6 receptor. Such peptides typically consist of 10-80, preferably 20-50, more preferably 20-40 amino acid residues.

IL-6 receptor peptides can be prepared by commonly known methods such as genetic engineering techniques or peptide synthesis on the basis of the amino acid sequence of a part or all of the region responsible for binding of IL-6 to the IL-6 receptor in the amino acid sequence of the IL-6 receptor after identifying such a region.

To prepare IL-6 receptor peptides by genetic engineering techniques, the DNA sequence encoding a desired peptide can be inserted into an expression vector and manipulated according to the methods for expressing, producing and purifying recombinant antibodies described above.

To prepare IL-6 receptor peptides by peptide synthesis, methods commonly used in peptide synthesis such as solid-phase synthesis or liquid-phase synthesis can be used.

Specifically, the method described in "Development of Pharmaceuticals II", volume 14, Peptide Synthesis, edited by Haruaki Yajima, Hirokawa Publishing Company 1991 can be followed. Solid-phase synthesis involves, for example, attaching an amino acid corresponding to the C-terminus of a peptide to be synthesized to a support insoluble in organic solvents, and elongating a peptide chain by alternately repeating a reaction in which amino acids protected at the a-amino group and side chain functional groups by a suitable protecting group are condensed one by one in the direction from the C-terminus to the N-terminus and a reaction in which the protecting group of the α-amino group of the amino acid or peptide attached to the resin are removed. Solid-phase peptide synthesis is mainly classified into the Boc method and the Fmoc method depending on the type of the protecting group used.

After the desired peptide is synthesized in this manner, it is deprotect d and cleaved from the support of the peptide chain take place. For cleavage from the peptide chain, hydrogen fluoride or trifluoromethanesulfonic acid can be typically used in the Boc method while TFA can be typically used in the Fmoc method. In the Boc method, the protected. peptide bound to the resin described above is treated in hydrogen fluoride in the presence of anisole, for example. Then, the protecting group is removed and the peptide is cleaved from the support and recovered. The recovered peptide is lyophilized to give a crude peptide. In the Fmoc method, on the other hand, deprotection and cleavage from the support of the peptide chain can be performed in TFA, for example, by procedures similar to those described above.

The resulting crude peptide can be isolated/purified by HPLC under optimal conditions eluting with a water/acetonitrile solvent system commonly used for purification of proteins. Fractions corresponding to peaks in the resulting chromatographic profile are collected and lyophilized. The peptide fractions purified in this matter are identified by mass spectrometry-based molecular weight analysis, amino acid composition analysis, or amino acid sequence analysis or the like.

As used herein, "antimetabolite" is not specifically limited so far as it is a substance that inhibits cellular reactions by a structure or function chemically similar to those of physiological metabolites necessary for nucleic acid synthesis or metabolic reaction, but especially preferably a nucleotide that inhibits DNA synthesis. Specifically, examples include thio-6-guanine, pentostatin, cytosine arabinoside, fluoro-5-uracil (5FU), fluorouridine-desoxyribose, capecitabine, gemcitabine, fludarabine and the like. Especially, cytosine analogs are preferred, among which gemcitabine is preferred. A preferred example of gemcitabine includes gemcitabine hydrochloride.

Therapeutic compositions for pancreatic cancer of the present invention can be used for treatment and/or prophylaxis of pancreatic cancer.

As used herein, "treatment of pancreatic cancer" refers to inhibition of development of pancreatic cancer, decrease in the incidence of pancreatic cancer, inhibition of the growth of pancreatic cancer cells, size reduction of pancreatic cancer tissue, improvement of symptoms of pancreatic cancer, inhibition of metastasis of pancreatic cancer, inhibition, reduction and elimination of pleural effusion or ascites caused by development of pancreatic cancer and the like.

As used herein, "combined administration" of an IL-6 inhibitor and an antimetabolite means that these drugs may be administered simultaneously or continuously or one may be administered first and then the other at an interval of time. When an anti-IL-6 inhibitor and an immunorepressor are administered, the doses can be appropriately adjusted depending on the weight, age, condition and the like of the subject to be treated, but when the IL-6 inhibitor is an anti-IL-6 antibody, the dose is, for example, 0.1-100 mg/kg/week or a dose providing an equivalent blood concentration, preferably 1-50 mg/kg/week or a dose providing an equivalent blood concentration, more preferably 5-10 mg/kg/week or a dose providing an equivalent blood concentration. When the antimetabolite is gemcitabine hydrochloride, the dose is, for example, 10-10000 mg/m$^2$/week or a dose providing an equivalent blood concentration, preferably 100-5000 mg/m$^2$/week or a dose providing an equivalent blood concentration, more preferably 500-1500 mg/m$^2$/week or a dose providing an equivalent blood concentration.

The mode of administration, dosing interval and dosage amount described above can be appropriately selected to provide a therapeutic effect comparable to the effect of the present invention. For example, the mode of administration, dosing interval and dosage amount providing an effect comparable to the examples above can be selected by measuring the blood concentration of each drug, and the mode of administration, dosing interval and dosage amount achieving blood concentrations comparable to the examples above are also included in the present invention.

The subject to which compositions or agents of the present invention are administered is a mammal. The mammal is preferably human.

Compositions or agents of the present invention can be administered orally or parenterally and systemically or topically in the form of pharmaceuticals. For example, intravenous injection such as drip injection, intramuscular injection, intraperitoneal injection, subcutaneous injection, suppositories, rectal formulations, oral enteric formulations and the like can be selected and the mode of administration can be appropriately selected depending on the age and condition of the patient.

Compositions or agents of the present invention may contain pharmaceutically acceptable carriers such as preservatives and stabilizers. Pharmaceutically acceptable carrier refers to a material that can be administered with the agents described above. Pharmaceutically acceptable materials include, for example, sterilized water, physiological saline, stabilizers, excipients, buffering agents, preservatives, surfactants, chelating agents (such as EDTA), binders and the like.

In the present invention, surfactants include nonionic surfactants, typical examples of which include, for example, sorbitan fatty acid esters such as sorbitan monocaprylate, sorbitan monolaurate, sorbitan monopalmitate; glycerin fatty acid esters such as glycerin monocaprylate, glycerin monomyristate, glycerin monostearate; polyglycerin fatty acid esters such as decaglyceryl monostearate, decaglyceryl distearate, decaglyceryl monolinoleate; polyoxyethylene sorbitan fatty acid esters such as polyoxyethylene sorbitan monolaurate, polyoxyethylene sorbitan monooleate, polyoxyethylene sorbitan monostearate, polyoxyethylene sorbitan monopalmitate, polyoxyethylene sorbitan trioleate, polyoxyethylene sorbitan tristearate; polyoxyethylene sorbitol fatty acid esters such as polyoxyethylene sorbitol tetrastearate, polyoxyethylene sorbitol tetraoleate; polyoxyethylene glycerin fatty acid esters such as polyoxyethylene glyceryl monostearate; polyethylene glycol fatty acid esters such as polyethylene glycol distearate; polyoxyethylene alkyl ethers such as polyoxyethylene lauryl ether; polyoxyethylene polyoxypropylene alkyl ethers such as polyoxyethylene polyoxypropylene glycol, polyoxyethylene polyoxypropylene propyl ether, polyoxyethylene polyoxypropylene cetyl ether; polyoxyethylene alkyl phenyl ethers such as polyoxyethylene onyl phenyl ether; polyoxyethylene hardened castor oils such as polyoxyethylene castor oil, polyoxyethylene hardened castor oil (polyoxyethylene hydrogenated castor oil); polyoxyethylene beeswax derivatives such as polyoxyethylene sorbitol beeswax; polyoxyethylene lanolin derivatives such as polyoxyethylene lanolin; polyoxyethylene fatty acid amides such as polyoxyethylene stearic acid amide, each of which has an HLB of 6-18, and the like.

Surfactants also include anionic surfactants, typical examples of which include, for example, alkyl sulfates having a C10-18 alkyl group such as sodium cetyl sulfate, sodium lauryl sulfate, sodium oleyl sulfate; polyoxyethylene alkyl ether sulfates having an average EO mole number of 2-4 and a C10-18 alkyl group such as sodium polyoxyethylene lauryl sulfate; alkyl sulfosuccinic acid ester salts having a C8-18 alkyl group such as sodium laurylsulfosuccinate; natural surfactants including, for example, lecithin; glycerophospholipids; sphingophospholipids such as sphingomyelin; sucrose fatty acid esters of C12-18 fatty acids, and the like.

Compositions or agents of the present invention can contain one or more of these surfactants in combination. Preferred surfactants used in formulations of the present invention include polyoxyethylene sorbitan fatty acid esters such as Polysorbate 20, 40, 60 or 80, especially Polysorbates 20 and 80. Polyoxyethylene polyoxypropylene glycols such as poloxamers (e.g. Pluronic F-68®) are also preferred.

The amount of the surfactants added depends on the type of the surfactants used, but it is typically 0.001-100 mg/mL, preferably 0.003-50 mg/mL, more preferably 0.005-2 mg/mL in the case of Polysorbate 20 or Polysorbate 80.

In the present invention, buffering agents include phosphoric acid, citrate buffer, acetic acid, malic acid, tartaric acid, succinic acid, lactic acid, potassium phosphate, gluconic acid, caprylic acid, deoxycholic acid, salicylic acid, triethanolamine, fumaric acid and other organic acids and the like, or carbonate buffer, Tris buffer, histidine buffer, imidazole buffer and the like.

Solution formulations may also be prepared by dissolving in an aqueous buffer known in the field of solution formulations. The concentration of the buffer is typically 1-500 mM, preferably 5-100 mM, more preferably 10-20 mM.

Moreover, compositions or agents of the present invention may contain proteins such as other low molecular mass polypeptides, serum albumin, gelatin or immunoglobulin; amino acids; sugars such as polysaccharides and monosaccharides or carbohydrates; and sugar alcohols.

In the present invention, amino acids include basic amino acids such as arginine, lysine, histidine, ornithine, or organic salts of these amino acids (preferably in the form of hydrochlorides, phosphates, i.e., amino acid phosphates). When free amino acids are used, preferred pH values are adjusted by adding a suitable physiologically acceptable buffering substance such as an inorganic acid, especially hydrochloric acid, phosphoric acid, sulfuric acid, acetic acid, formic acid or a salt thereof. Here, it is especially advantageous to use phosphoric acid salts because especially stable lyophilized products can be obtained. It is especially advantageous when preparations contain substantially no organic acid such as malic acid, tartaric acid, citric acid, succinic acid or fumaric acid or when no corresponding anion (such as malate ion, tartrate ion, citrate ion succinate ion or fumarate ion) exists. Preferred amino acids are arginine, lysine, histidine, or ornithine. Moreover, acidic amino acids such as glutamic acid and aspartic acid and salts thereof (preferably sodium salts), or neutral amino acids such as isoleucine, leucine, glycine, serine, threonine, valine, methionine, cysteine or alanine, or aromatic amino acids such as phenylalanine, tyrosine, tryptophan or its derivative N-acetyltryptophan can also be used.

In the present invention, sugars such as polysaccharides and monosaccharides or carbohydrates include, for example, dextran, glucose, fructose, lactose, xylose, mannose, maltose, sucrose, trehalose, raffinose and the like.

In the present invention, sugar alcohols include, for example, mannitol, sorbitol, inositol and the like.

When compositions or agents of the present invention are in the form of aqueous solutions for injection, they can be mixed with isotonic solutions containing, for example, physiological saline, glucose or other adjuvants (e.g., D-sorbitol, D-mannose, D-inannitol, sodium chloride). The aqueous solutions can also be used in combination with suitable solubilizers (e.g., alcohol (ethanol, etc.), polyalcohol (propylene glycol, PEG, etc.), nonionic surfactants (Polysorbate 80, HCO-50) and the like).

If desired, they may further contain diluents, solubilizers, pH modifiers, soothing agents, sulfur-containing reducing agents, antioxidants and the like.

In the present invention, sulfur-containing reducing agents include, for example, sulfhydryl-containing compounds such as N-acetylcysteine, N-acetylhomocysteine, thioctic acid, thiodiglycol, thioethanolamine, thioglycerol, thiosorbitol, thioglycolic acid and salts thereof, sodium thiosulfate, glutathione, and thioalkanoic acids having 1 to 7 carbon atoms.

In the present invention, antioxidants include, for example, erythorbic acid, dibutylhydroxytoluene, butylhydroxyanisole, α-tocopherol, tocopherol acetate, L-ascorbic acid and salts thereof, L-ascorbyl palmitate, L-ascorbyl stearate, sodium bisulfite, sodium sulfite, triamyl gallate, propyl gallate or chelating agents such as disodium ethylenediamine tetraacetate (EDTA), sodium pyrophosphate and sodium metaphosphate.

If desired, the compositions or agents can be encapsulated into microcapsules (microcapsules of hydroxymethylcellulose, gelatin, poly[methylmethacrylic acid] or the like) or formulated into colloidal drug delivery systems (liposomes, albumin microspheres, microemulsions, nanoparticles and nanocapsules, etc.) (see "Remington's Pharmaceutical. Science 16$^{th}$ edition", Oslo Ed., 1980 or the like). Further, methods for formulating compositions or agents into sustained release systems are also known and can be applied to the present invention (Langer et al., J. Biomed. Mater. Res. 1981, 15: 167-277; Langer, Chem. Tech. 1982, 12: 98-105; U.S. Pat. No. 3,773,919; European Patent Application published as (EP) 58,481; Sidman et al., Biopolymers 1983, 22: 547-556; EP 133,988).

Pharmaceutically acceptable carriers used are selected as appropriate or in combination from, but not limited to, the above list depending on the dosage form.

The subject to which compositions or agents of the present invention are administered refers to a living body to which the compositions or agents of the present invention are administered or a part in the living body. Living bodies include, but not specifically limited to, animals (e.g., human, domestic animal species, wild animals).

A part in the living body is not specifically limited to, but preferably includes an affected site or the like.

As used herein, "administration" includes oral or parenteral administration. Oral administration includes administration in the form of oral formulations, and dosage forms such as granules, powders, tablets, capsules, solutions, emulsions, or suspensions can be selected as oral formulations.

Parenteral administration includes administration in the form of injections, and injections include subcutaneous injections, intramuscular injections, or intraperitoneal injections, etc. Moreover, agents of the present invention can also be topically administered to an area to be treated. For example, they can be administered by topical injection during surgical operation or the use of a catheter.

When carrying out methods of the present invention, an agent of the present invention can be administered as a part of a pharmaceutical composition with at least one additional drug (for example, other perineural invasion inhibitors or other therapeutic agents for pancreatic cancer). In one embodiment, an agent of the present invention and another agent may be administered substantially at the same time.

All of the prior art documents cited herein are incorporated herein by reference.

EXAMPLES

The following examples further illustrate the present invention without, however, limiting the invention thereto, Various changes and modifications can be made by those skilled in the art, and such changes and modifications are also included in the present invention.

Example 1: Effect of Combined Administration of Gemcitabine Hydrochloride and Tocilizumab on Pancreatic Cancer A chemotherapy-naive patient having progressive/metastatic pancreatic cancer and showing CRP>=2.0 mg/dL (CRP: C-reactive protein that correlates with the intensity of inflammatory response) was treated with gemcitabine hydrochloride and a humanized IL-6 receptor antibody (tocilizumab).

Figure 1:
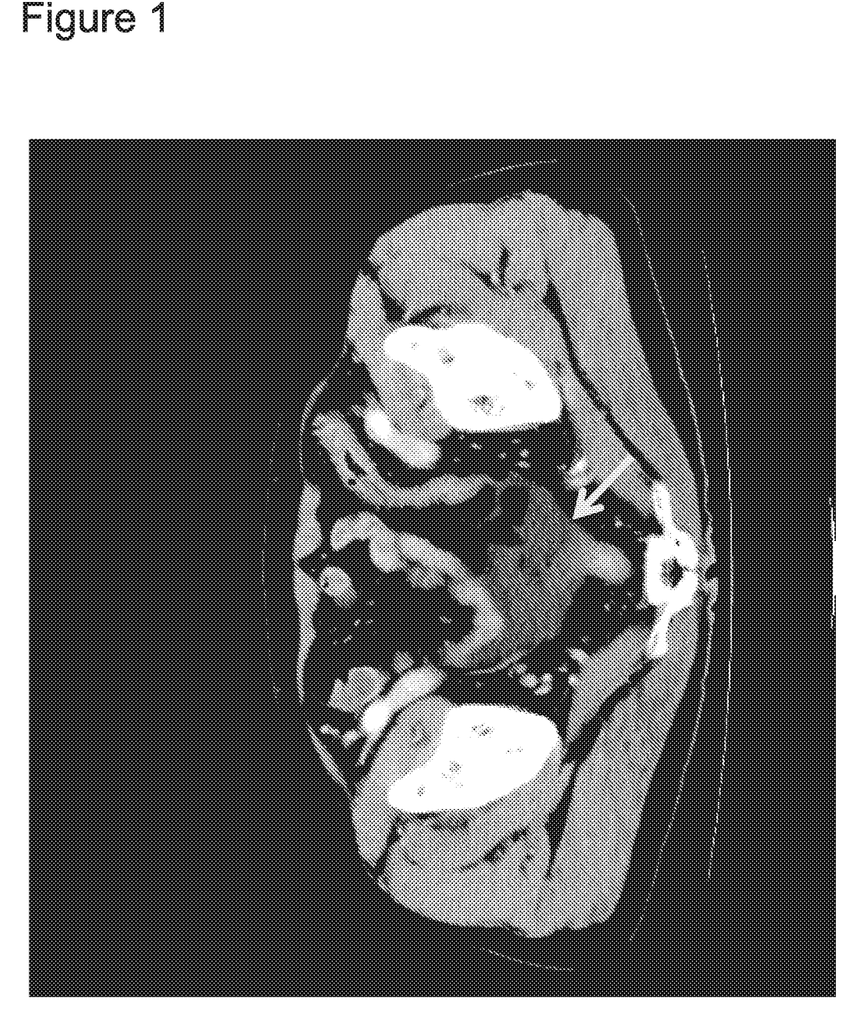
FIG. 1 shows a CT image of ascites of a pancreatic cancer patient before gemcitabine hydrochloride and tocilizumab are administered in combination.

A male at age 72 with no history of smoking having pancreatic body cancer of Stage IV as defined by the TNM classification of UICC[1]) had metastatic lesions in the liver, lymph nodes, ascites and peritoneum and had evident ascites as shown in FIG. 1. This case had a CRP of 3.28 mg/dL immediately before administration and also suffered from hyperlipidemia and chronic atrophic gastritis as complications. This patient was treated with gemcitabine hydrochloride and tocilizumab in combination. Gemcitabine hydrochloride was administered by intravenous drip injection at 1000 mg/m$^2$ expressed as gemcitabine over 30 min once a week for 3 weeks followed by the 4th week of washout. This cycle was repeated. Tocilizumab was administered by intravenous drip injection at 8 mg/kg over about 60 min every 2 weeks. Depending on the condition of the patient, gemcitabine or tocilizumab was withdrawn or reduced. For PK (pharmacokinetics) analysis, medication was started on day 1 for gemcitabine hydrochloride and on day 2 for tocilizumab. The subsequent medications were each performed on the same day.

Figure 2:
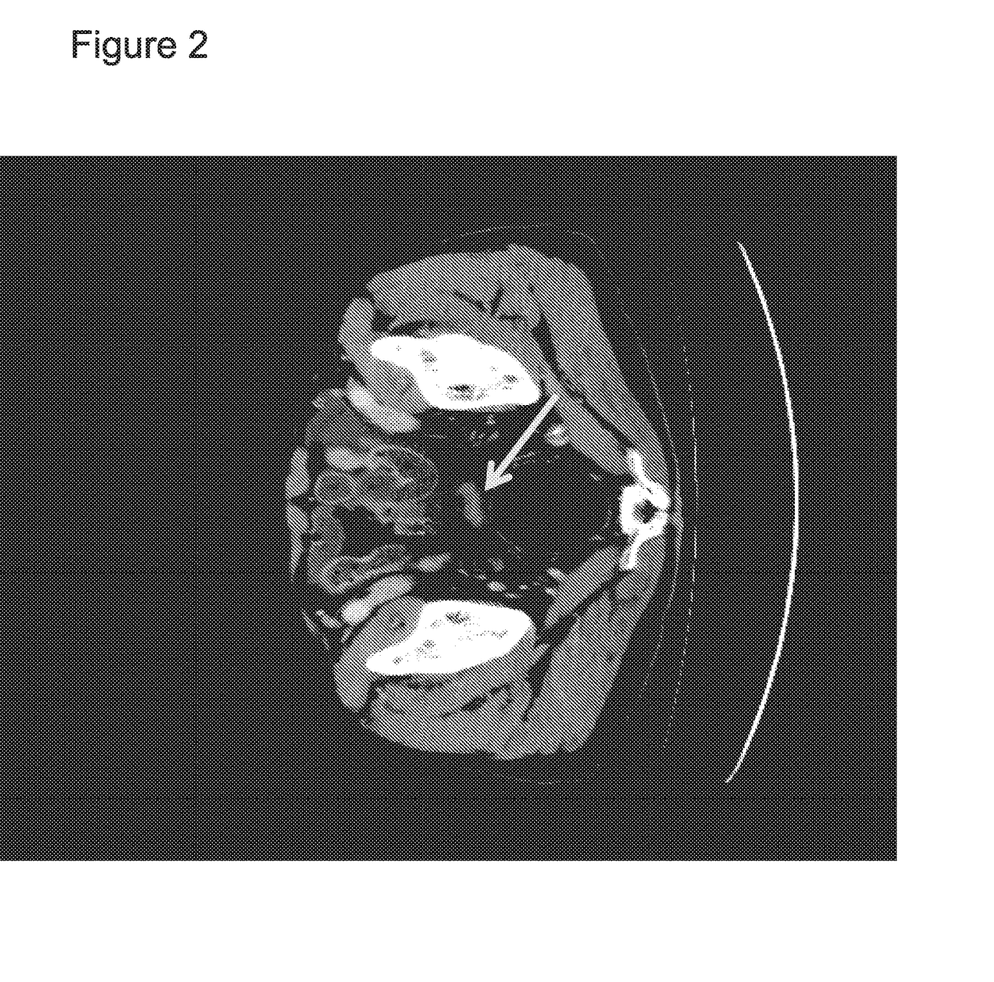
FIG. 2 shows a CT image of ascites of the pancreatic cancer patient 8 weeks after starting combined administration of gemcitabine hydrochloride and tocilizumab.
Figure 3:
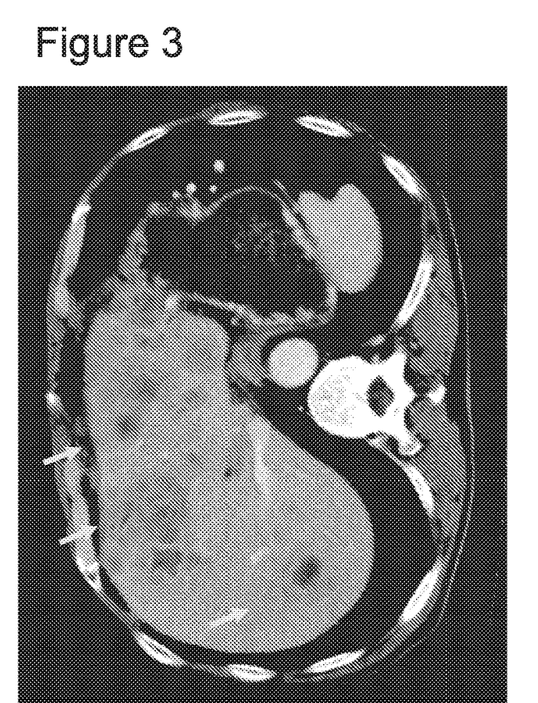
FIG. 3 shows a CT image of metastatic lesions in the liver of the pancreatic cancer patient before gemcitabine hydrochloride and tocilizumab are administered in combination.
Figure 4:
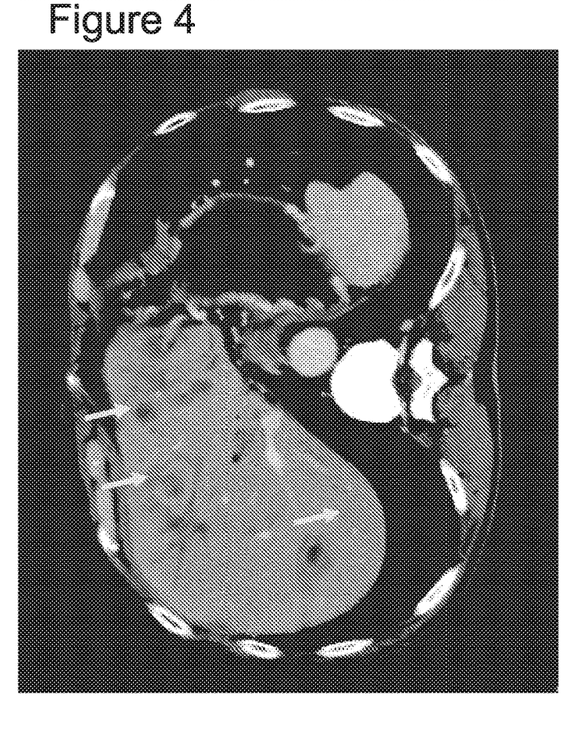
FIG. 4 shows a CT image of metastatic lesions in the liver of the pancreatic cancer patient 8 weeks after starting combined administration of gemcitabine hydrochloride and tocilizumab.

As for CRP levels that have been reported to be associated with very poor prognosis when they are 2.0 mg/dL or more[2]), they decreased to 0.66 mg/dL after 1 week and decreased to 0.44 mg/dL falling within the normal range (0.5 mg/dL or less) after 2 weeks. CRP remained in the normal range until the end of treatment. Ascites was remarkably reduced after 4 weeks, and further reduced to the extent that it was scarcely observed after 8 weeks as shown in FIG. 2. Primary and metastatic tumor lesions were reduced by 24% after 8 weeks, and 31% after 12 weeks. Metastatic lesions in the liver were also evidently reduced after 8 weeks (FIG. 4) as compared with before treatment (FIG. 3).

Tumor markers showed CEA of 112.6 ng/mL and CA19-9 of 47700 U/mL before treatment, but decreased to 20.4 ng/mL and 7900 U/mL after 8 weeks, and to 9.8 ng/mL and 8820 U/mL after 12 weeks. No serious side effect was observed.

We previously closely analyzed clinical performance of gemcitabine hydrochloride monotherapy in progressive/metastatic pancreatic cancer patients and found that the average change in tumor size 3 months after the start of monotherapy (analyzable cases: 25 cases) was an increase of 36.0% (95% confidence interval: 4.6-67.4%) and that ascites was not eliminated during the monotherapy of 3 months (analyzable cases: 29 cases). Thus, the tumor reducing effect and ascites eliminating effect observed in one case of combination therapy were not observed with monotherapy.

These results showed that combined administration of gemcitabine and tocilizumab had an excellent therapeutic effect as proved by reduction in pancreatic cancer and metastatic lesions. Improvements of pancreatic cancer also provided an ascites eliminating effect that could not be observed with monotheraphy.

1) Sobin L H, Wittekind C L, editors. TNM classification of malignant tumors, 6th edition. New York: John Wiley & Sons, 2002.
2) Shuichi Mitsunaga, Masafumi Ikeda, Kohei Nakachi et al.: Effectiveness of serum CRP levels as an indicator of cachexia in patients having unresectable pancreatic cancer. The 40th Annual Academic Meeting of the Japan Pancreas Society, 2009.

INDUSTRIAL APPLICABILITY

In the present invention, it was shown that an excellent therapeutic effect against pancreatic cancer can be obtained by administering an IL-6 inhibitor and an antimetabolite in combination. Moreover, it was also shown that metastatic lesions from human pancreatic cancer can be reduced and ascites can be eliminated.

The invention claimed is:
1. A method for reducing pancreatic cancer lesions, comprising administering a therapeutically effective amount of an anti-interleukin-6 (IL-6) receptor antibody and gemcitabine or a salt thereof to a subject in need thereof, wherein the size of pancreatic cancer tissue in the subject is reduced.

2. The method of claim 1, wherein the anti-IL-6 receptor antibody is a chimeric antibody, a humanized antibody or a human antibody.

3. The method of claim 1, wherein gemcitabine or a salt thereof is gemcitabine hydrochloride.

4. The method of claim 1, wherein ascites of the subject being treated are reduced.

5. The method of claim 1, wherein the anti-IL-6 receptor antibody is tocilizumab.

6. The method of claim 1, wherein the anti-IL-6 receptor antibody is tocilizumab and the gemcitabine or a salt thereof is gemcitabine hydrochloride.

* * * * *